United States Patent [19]

Ruhenstroth-Bauer

[11] Patent Number: 5,624,373
[45] Date of Patent: Apr. 29, 1997

[54] METHOD AND APPARATUS FOR INFLUENCING SUCH CHARACTERISTICS OF A BIOLOGICAL MATERIAL WHICH CORRELATE WITH THE OCCURRENCE OF CERTAIN ATMOSPHERICS

[76] Inventor: Gerhard Ruhenstroth-Bauer, Spietzelbergerstrasse 11, D-82166 Gräfeling, Germany

[21] Appl. No.: 298,751

[22] Filed: Aug. 31, 1994

[30] Foreign Application Priority Data

Sep. 6, 1993 [DE] Germany .................. 43 29 884.2

[51] Int. Cl.⁶ .................................................. A61N 1/44
[52] U.S. Cl. ............................................................. 600/9
[58] Field of Search ........................... 600/9, 10, 13–15

[56] References Cited

U.S. PATENT DOCUMENTS

| | | | |
|---|---|---|---|
| 4,545,368 | 10/1985 | Rand et al. | 600/13 X |
| 4,631,957 | 12/1986 | Ruhentroth-Bauer | 128/898 X |
| 4,665,898 | 5/1987 | Costa et al. | 600/14 |
| 5,014,699 | 5/1991 | Pollack et al. | 600/9 |
| 5,045,050 | 9/1991 | Liboff et al. | 600/9 |

FOREIGN PATENT DOCUMENTS

| | | |
|---|---|---|
| 0005713 | 5/1979 | European Pat. Off. . |
| 4018063A1 | 12/1991 | Germany . |
| 4133209A1 | 4/1993 | Germany . |
| 1079254 | 3/1984 | U.S.S.R. . |

*Primary Examiner*—Angela D. Sykes
*Assistant Examiner*—Samuel G. Gilbert
*Attorney, Agent, or Firm*—Jones, Tullar & Cooper, P.C.

[57] ABSTRACT

A method and apparatus for influencing a biological material, both being intended to influence such characteristics are correlated with the occurrence of natural atmospherics, i.e., the proliferation rate of C6-glioma cells and the survival time of Yoshida-ascites-hepatoma rats. For this purpose, signals representing the time history of the magnetic field of certain natural atmospherics are stored, which are identified by means of distinctly pronounced frequency fractions, e.g., 10 kHz. Using these signals, corresponding magnetic field variations are reproduced as artificial atmospherics. Reproduction is effected, e.g., in a Helmholtz coil. The biological material is exposed to this magnetic field.

8 Claims, 5 Drawing Sheets

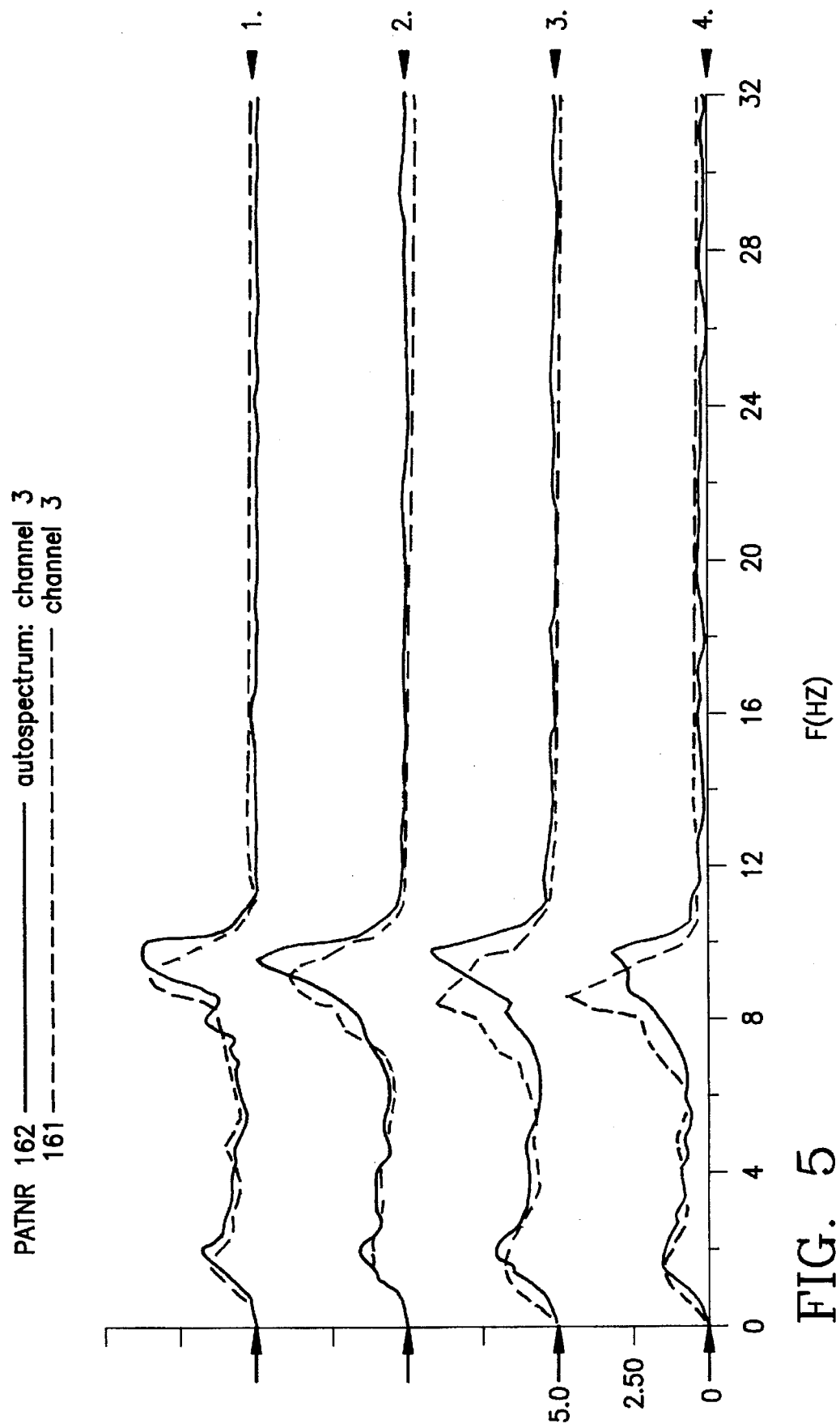

METHOD AND APPARATUS FOR INFLUENCING SUCH CHARACTERISTICS OF A BIOLOGICAL MATERIAL WHICH CORRELATE WITH THE OCCURRENCE OF CERTAIN ATMOSPHERICS

BACKGROUND OF THE INVENTION

It is known that certain electromagnetic oscillatory phenomena occurring in connection with meteorological conditions are correlated with variations of biological and pathological parameters.

Characterization of the respective pulses (Very-Low-Frequency Atmospherics; hereinafter: atmospherics), particularly according to frequency and wave form, has been undertaken, among others, by H. Baumer and J. Eichmeier in: Eine Anlage zur Registrierung der Atmospherics bei 10 und 27 kHz, Archiv für Meteorologie, Geophysik und Bioklimatologie [a System for Recording Atmospherics at 10 and 27 KHz, Archieves for Meterology Geophysics and Bioclimatology], Ser. A, 29, 143 to 155 (1980), and by W. Sönning, H. Baumer and J. Eichmeier in: Die Atmospherics-Aktivität bei 10 und 27 kHz als Indikator für die Dynamik der troposphärischen Wettervorgänge [Atmospherics Activity at 10 and 27 KHz as an indicator for the Dynamics of Tropospheric Weather Processes], Archives For Meteorology, Geophysics and Bioclimatology, Ser. B, 29, pp. 299–312 (1981). Atmospherics are short-time pulses in the form of damped oscillations. Their respective duration comprises approximately 5 to 6 half-waves. They are a mixture of different frequencies. Using measuring techniques, atmospherics have been determined by Baumer according to their predominant frequency fraction of e.g. 6, 8, 10, 12 and 28 kHz. They will therefore be designated in the following as "according to Baumer"=atB.

A relationship has already been established between the frequency of occurrence of some definite atmospherics and various biological parameters. H. Baumer, in: Die Meteotropie eines Dichromat-Gelatinesystems, Technischer Informationsdienst des Bundesverbandes Druck e. V. [The Meteotropy of a Dichromatic-Gelatine System, published by the Technical Information Service of the Federal Association for Printing, Registered Assocation] II/1982, pp. 1 to 17, describes the difference in pulse rates in the 10 kHz and 28 kHz ranges and how they distinctly correlate with the diffusion behaviour of gelatine, which, in turn, influences the production process of rotogravure forms; cf. also H. Baumer and J. Eichmeier: Relationship between the Pulse Rate of Impulsstrahlung and the Diffusion Time of Ions in Gelatine Films, Int. J. Biometeor. 1980, Vol. 24, No. 3, pp. 271 to 276, as well as H. Baumer and J. Eichmeier: The Biophysically Active Wave Forms of Impulsstrahlung Incident on Gelatine Films, Int. J. Biometeor. 1982, Vol. 26, pp. 85–90.

The correlation of atmospherics with certain diseases such as epilepsy and cardiac infarction, for which some relationship with meteorological conditions had already been supposed before, has been described in the EP 0 120 991 A2 (U.S. Pat. No. 4,631,957); cf. also G. Ruhenstroth-Bauer, H. Baumer et al.: Epilepsy and Weather: A significant Correlation Between the Onset of Epileptic Seisures and Specific Impulsstrahlung - A Pilot Study, Int. J. Biometeor. 1984, Vol. 28, No. 4, pp. 333–340, and G. Ruhenstroth-Bauer, H. Baumer, among others: Myocardial Infarction and the Weather; A significant Positive Correlation between the Onset of Heart Infarct and 28 kHz Impulsstrahlung - A Pilot Study, Clin. Cardiol., 8, pp. 149–151 (1985).

Furthermore, a correlation has been found to exist between the 8 kHz and 10 kHz atmospherics and inflammatory processes in rats; see G. Ruhenstroth-Bauer, O. Rosing, and H. Baumer, Naturwissenschaften (Natural Sciences) 73, p. 625 (1986).

In addition, an important correlation between natural atmospheric spectra and the in vitro incorporation of ($^3$H)-thymidine into the nuclear DNA of C6-glioma-cells has been stated; cf. Vogl, G. Hoffmann, B. Stöpfel, H. Baumer, O. Kemsky and G. Ruhenstroth-Bauer: Significant Correlations Between Atmospheric Spectra According to Baumer and the in vitro Incorporation of ($^3$H)-Thymidine into the Nuclear DNA of C6-Glioma-Cells, FEBS Letters, Vol. 288, No. 1, 2, pp. 244–246 (1991).

A summary of the relations between atmospherics and biological and pathological parameters known so far is to be found in G. Hoffmann, S. Vogl, H. Baumer, O. Kemsky and G. Ruhenstroth-Bauer: Significant Correlations Between Certain Spectra of Atmospherics and Different Biological and Pathological Parameters, in: Int. J. Biometeorol. (1991) 34, pp. 247–250.

It is not possible as yet, however, to detect any relation of causality between the occurrence of those atmospherics and the described biological and pathological parameters.

SUMMARY OF THE INVENTION

It is an object of the present invention to provide a method and an apparatus allowing for a direct exercise of influence on such characteristics of biological materials which correlate with the occurrence of atmospherics.

A method is provided for influencing such characteristics of a biological material as are correlated with the occurrence of natural atmospherics. According to the method the time history of the magnetic field of natural atmospherics is received and stored, artificial atmospherics are generated by reproducing the stored magnetic field within a coil arrangement, and the biological material is introduced into the magnetic field. According to the apparatus a memory for storing signals representing the time history of portions of natural atmospherics is provided along with means for randomized readout of signals stored in the memory. A magnetic-field generator, the field strength of which is essentially homogeneous within a determined volume, and which generates a magnetic field representing artificial atmospherics, using signals readout of the memory is employed along with means within the homogenous field for introducing the biological material.

BRIEF DESCRIPTION OF THE DRAWINGS

The present invention will be described in more detail with reference to the attached drawings, in which:

FIG. 5 shows the offset of the electroencephalogram (EEG) with test persons influenced by artificial atmospherics.

DETAILED DESCRIPTION

The influence exercised on biological material by artificial atmospherics will be described in the following for three cases, i.e. (1) the proliferation rate of C6-glioma cells, (2) the survival time of Yoshida-ascites-hepatoma rats, and (3) the EEG offset with human test persons.

Figure 2A:
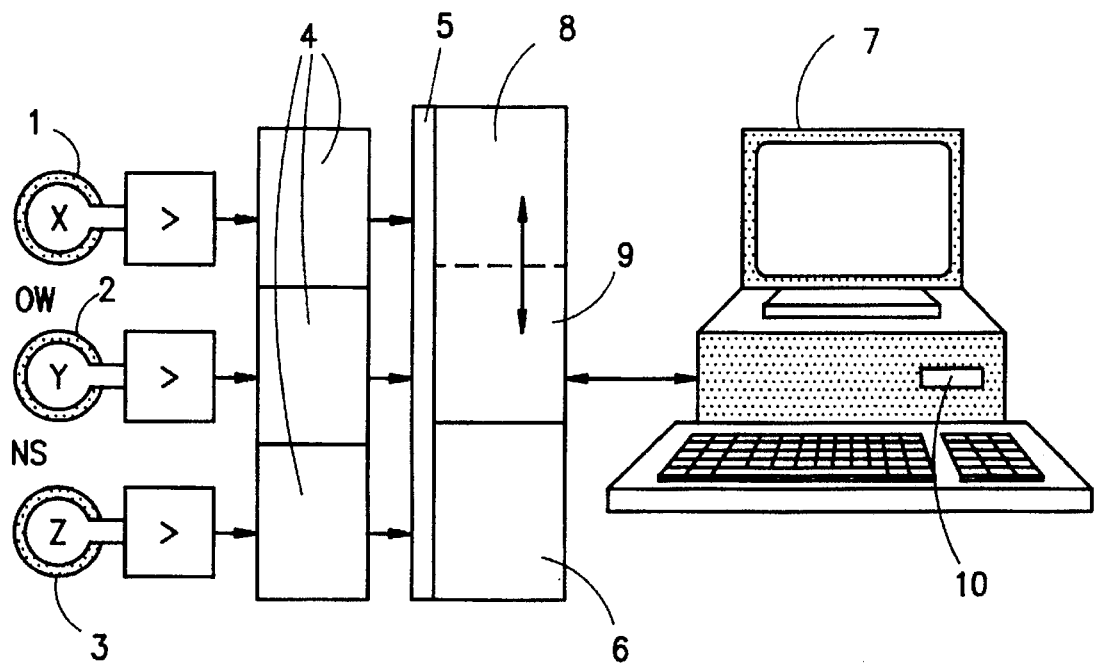
FIG. 2(a) shows an embodiment of a device for receiving and storing atmospherics.

At times when natural atmospherics having a particularly important 10 kHz frequency fraction were observed, the atmospherics were recorded using a specially designed wideband measuring system according to FIG. 2(a).

This recording device has been described in the literature by H. L. König, R. Kulzer and H. -D Betz in: "Aufbau einer Meßstation zur breitbandigen Untersuchung von VLF-Impulsstrahlung", Kleinheubacher Berichte, Vol. 35, (1992), pp. 387 to 394, and in published German Patent Application P 41 33 209.1 A1. Therein the magnetic field vector is recorded with a system comprising three antennas 1, 2, 3 disposed in mutually perpendicular arrangement and labelled with components X, Y, Z and with the cardinal points (OW=east-west, NS=north-south, Z=vertical). In order to avoid spectral overlapping in the subsequent discrete-time signal processing operation, each signal is submitted to band limitation in an associated filter 4. The 3-db points of the filters are localized at 1 kHz and at 100 kHz. From there, the signals go to an A/D converter 5.

The A/D converter is controlled through a trigger logic 8 programmable from a computer 7. When the trigger logic detects the incidence of atmospherics, the latter, or more properly speaking, their associated digitized measuring values, are transmitted to the computer 7 where they are processed and then stored in a further memory, e.g. on a floppy disk or a moving-head hard disk. Processing in the computer includes, among other things, mathematical evaluation of the absolute value of the magnetic field vector from the measured components. The memory is designated in FIG. 2(a) by reference numeral 10. The trigger logic 8, the memory 6 and a timer 9 are generally disposed on one circuit board, and they are therefore represented as one unit. Recognition of atmospherics by the trigger logic is based on exceeding certain threshold values and on the characterization of frequency fractions and wave forms according to Baumer (see above), though the present invention thereby properly detects further electromagnetic influences just through this reproduction.

Figure 1A:
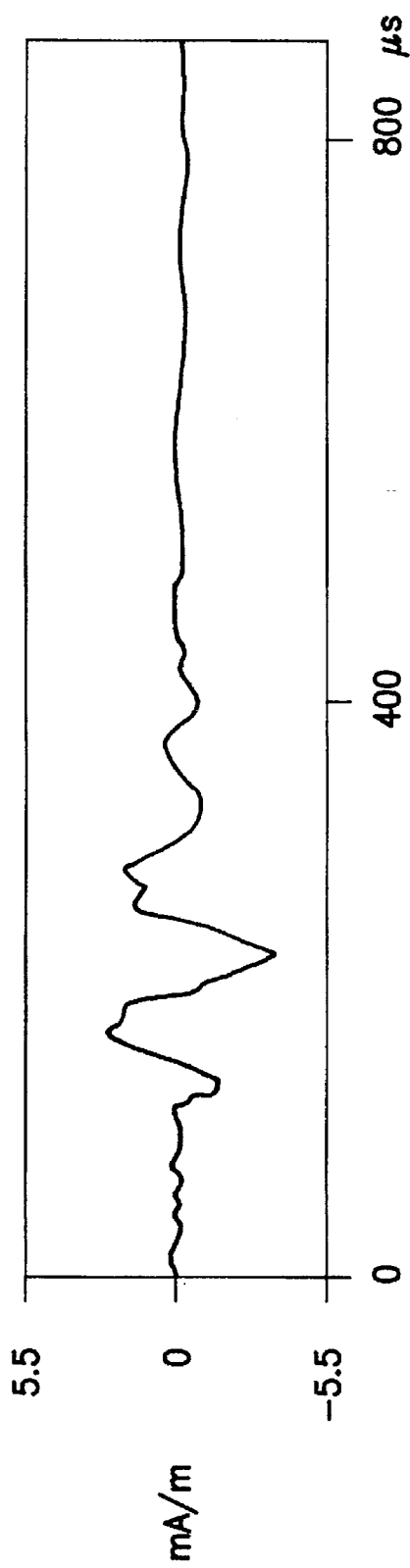
FIG. 1(a) shows the time history of the magnetic field strength, in A/m×10$^{-3}$ of typical VLF atmospherics as a function of time.

FIG. 1(a) shows the shape versus time of detected atmospherics as stored. Over a period of 820 microseconds, the development of magnetic field strength has been plotted in $10^{-3}$ A/m.

Figure 1B:
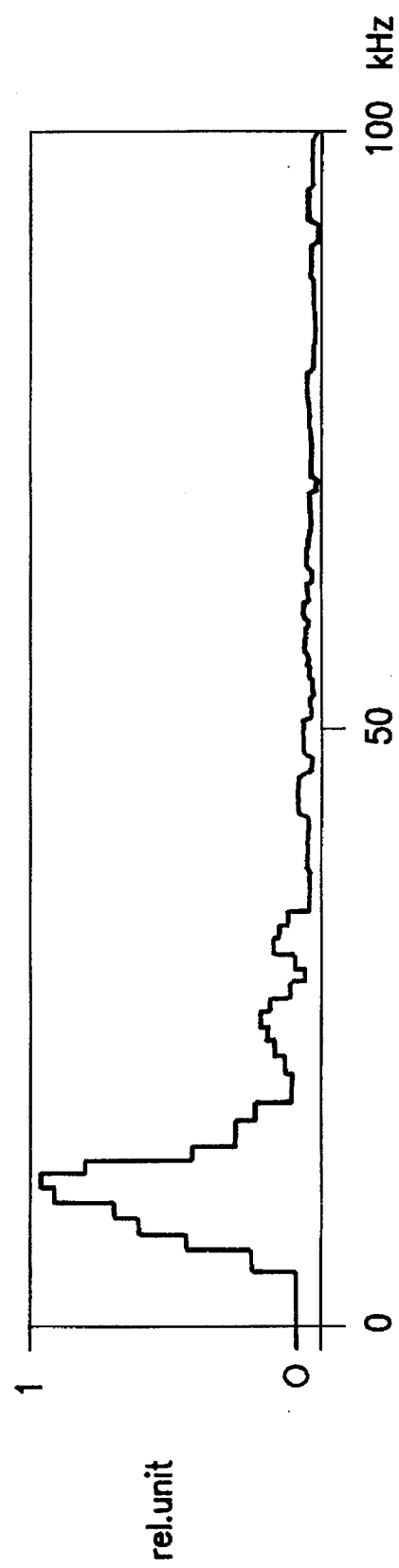
FIG. 1(b) is the frequency spectrum of the atmospherics shown in FIG. 1(a) between 0 kHz and 100 kHz.

FIG. 1(b) shows the associated standardized frequency spectrum in the range of 0 to 100 kHz. It indicates that the predominant frequency fraction is in the range of 10 kHz. This is a typical example of atmospherics atB. At the same time, however, the frequency analysis according to FIG. 1(b) shows that still further frequency fractions are present. These additional fractions are similarly detected and stored by the described device. In order to perform the process of the present invention, the 10 kHz atmospherics atB shown in FIGS. 1(a) and 1(b) will be reproduced.

Figure 2B:
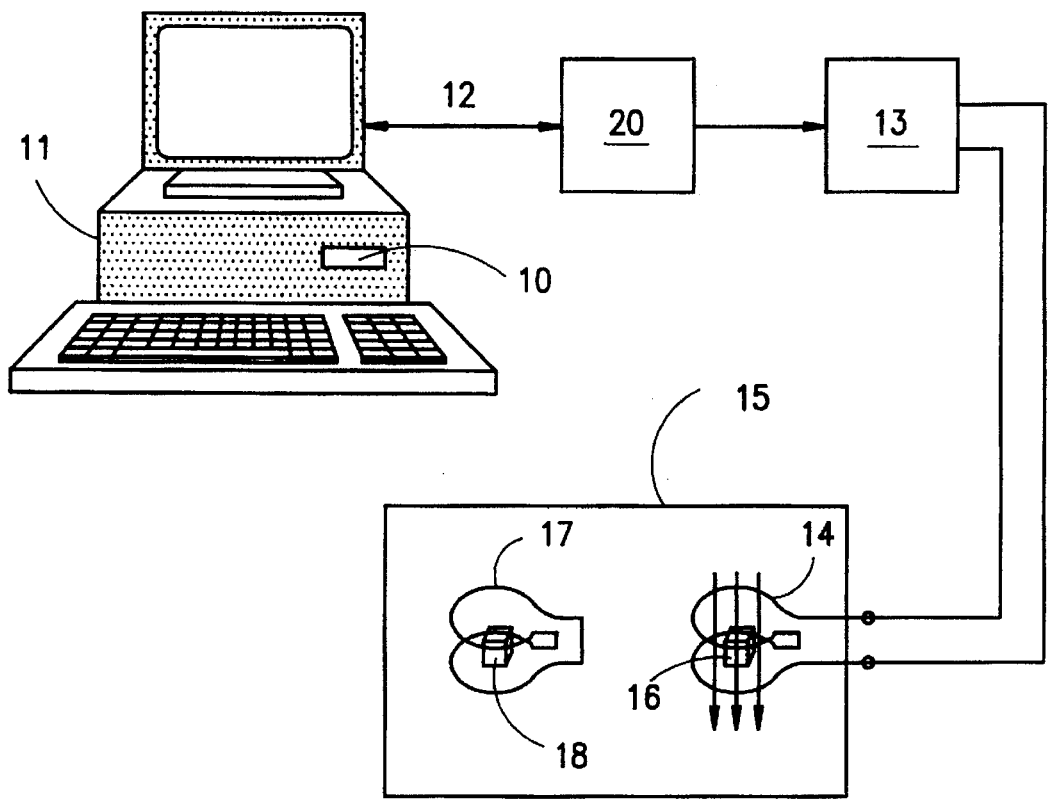
FIG. 2(b) shows an embodiment of a device for generating artificial atmospherics and for irradiating C6-glioma cells.

The required reproducing equipment is shown in FIG. 2(b). The signal shapes stored before e.g. on a floppy disk in the computer 7 are transmitted to a programmable signal generator 20 through the XT-bus 12 by a computer 11, into which the above mentioned transportable memory 10 is incorporated or into the memory of the atmospherics stored before on said memory 10 are transferred. In principle, computer 11 can be a computer similar to computer 7. Recording and reproduction may, however, be effected at different times and at different places. Computer 11 initiates randomized readout of the signal shape of the atmospherics stored in the memory 10 by the signal generator 20, at time intervals varying between 50 to 150 milliseconds. The shape of the magnetic field of the absolute value of the atmospherics is simulated with a Helmholtz coil 14. As the current flowing in the Helmholtz coil 14 is the controlling quantity (the magnetic field generated is proportional to the current), this must first be impressed on the output signal of the signal generator 20 by means of a voltage-to-current converter 13. Thereby an essentially homogeneous magnetic field is generated within the Helmholtz coil 14, the shape and frequency characteristics of which are equal to those of the recorded natural atmospherics. Thus the atmospherics are reproduced. Hence artificial atmospherics are generated.

The Helmholtz coil 14 has a diameter of approx. 20 cm and a distance between coil sections of 10 cm. These indications apply to the configuration used for examining the C6-glioma cells (see below, item 1).

1. C6-Glioma Cells

In order to test the influence of the magnetic field—indicated by the arrows in FIG. 2(b)—of artificial atmospherics produced in this way, C6-glioma cells were placed into the space between the coils as a sample 16. The entire system was arranged in an incubator 15. Care must be taken that the sample 16 is placed in the center line of the Helmholtz coil 14, since this is the most homogeneous portion of the magnetic field. The non-homogeneity of the magnetic field strength inside the Helmholtz coil was 40 to 200% of the desired value in a practical embodiment. The nominal maximum magnetic field strength was 100 mA/m and 25 mA/m respectively. In comparison with this, the average magnetic field strength of natural atmospherics is approx. 8 mA/m.

The cell culture of C6-glioma cells was produced as follows: The C6-glioma cells were growing as a monolayer in Petri dishes (100.20 mm, Falcon 3003, Becton Dickinson, Plymouth, England) on Dulbecco Modified Minimum Essential Medium (DMEM; Boehringer Mannheim, Germany) with 25 mM of hydrocarbonate. The medium was completed with 10% of fetal calf serum (FCS; Boehringer Mannheim). 100 IU/ml of penicillin G 50 and 50 µg/ml of streptomycin were added to prevent bacterial infections. The cells were cultivated in a conventional incubator at 37° C. in moistened ambient air with 5% of $CO_2$. The cells were transferred three times a week. For each experiment, eight (8) Petri dishes provided two days after transferring and completely covered with cells were used. The cells were reaped by momentary incubation with 0.06% trypsin/0.02% EDTA, suspended in PBS (phosphate buffered saline), resuspended in an FCS containing medium, pooled and then sowed in equal quantities into 24 Petri dishes (60.25 mm, Falcon 3004, Becton Dickinson).

For performing these experiments, 2 groups A and B of 12 Petri dishes each were introduced into the Helmholtz coil 14 or respectively into another Helmholtz coil 17 in the incubator 15 as samples 16 and 18. Both groups were placed at as great a distance as possible from each other. The Helmholtz coil 14 containing group B was electromagnetically excited; the other Helmholtz coil 17 containing group A as the sample 18 was shorted to serve for control. After an incubation time of 24 hours, the medium was removed, and the cultures were washed with PBS. Then 5 ml of DMEM with 10% of FCS and $^3$H-thymidin ($3.7 \times 10^4$ Bq/ml; Amersham Buchler, Brunswick, Germany) were added to each dish. After another hour of incubation of the cultures inside the coil, the medium was carefully removed. The cells were washed with ice-cold PBS and the dishes were out on ice. Then the cells of each Petri dish were reaped separately in the above described way, and the cells were frozen up to the time of determining the DNA content and the $^3$H-thymidin incorporation. The specific radioactivity in cpm/μg of DNA was determined for each sample, and the mean value was computed for the two groups A and B. The result from group B was evaluated as a percentage of the one obtained from Group A (control group).

In the course of these experiments, three series of experimental runs were carried out. In one control run comprising 10 tests, no one of groups A and B was exposed to artificial atmospherics. In two test runs, group B was exposed to atmospherics having a predominant spectral component of 10 kHz with maximum magnetic field strengths of 100 mA/m (13 tests) and 25 mA/m (4 tests).

The first step for determining the specific radioactivity was extracting the pulse-marked DNA from the C6-glioma cells according to Weinbren and Woodward (Brit. J. exper, Path. 45, pp. 442–449, 1964).

After unfreezing the frozen cell samples (each suspended in 1 ml of PBS), 3 ml of cooled 0.25M perchloric acetic acid (PCA) were added. Then the samples were held at 4° C. for 30 minutes. Subsequently the cells were centrifuged at 4000× g for 15 minutes, and the pellets were agitated in 0.5 ml of 0.5M NaOH at room temperature for 30 minutes. After this, 4.5 ml of 0.5M PCA were added and the samples allowed to stand again at 4° C. for at least 30 minutes (or overnight). The test tubes were centrifuged at 4000× g for 15 minutes, and the pellets were boiled in 3 ml of 0.5M PCA at 95° C. for 20 minutes. After centrifuging at 4000× g for 10 minutes, the supernatants were collected and stored. This process was repeated, the two supernatants were combined and their ($^3$H)-thymidin content as well as their DNA content was determined according to Burton (Burton, K., Biochem. 62 (1956), pp. 315–323). 1 ml of a solution of diphenylamine in acetic acid was added to 0.5 ml of the supernatant. The samples were stored at room temperature in the dark for 22 to 24 hours. Then the extinction at 590 nm was measured and the DNA content was computed.

The specific radioactivity was obtained as the quotient of the values of the radioactivity and of the DNA, expressed in dpm/μg of DNA.

From the test results without irradiation, it happened that the results differed by 3.9±1.4% (mean value±the standard deviation) with regard to the incorporation of ($^3$H)-thymidin into the nuclear DNA, depending on their positioning inside the incubator. This means that even without irradiation there was a definite position within the incubator (i.e. on its base) where a higher proliferation rate of cells was obtained than in other positions. Therefore this value (3.9±1.4%) was subsequently deducted from the test results in order to compensate mathematically for any influences from magnetic fields possibly existing inside the incubator.

For group B (irradiation with artificial atmospherics having a predominant spectral component of 10 kHz), a proliferation rate of −4.5±3.7% (p−0.05) at a field strength of 100 mA/m, and a proliferation rate of 6.1±1.8% at a field strength of 25 mA/m was obtained relative to A. When correcting these values by the above indicated value, which must be taken into account to compensate influences due to the incubator, the following values are obtained.

| Field Strength | Proliferation Rate |
| --- | --- |
| 0 | 0 |
| 25 mA/m | 2.2 ± 1.8% |
| 100 mA/m | −8.4 ± 3.7% |

Figure 3:
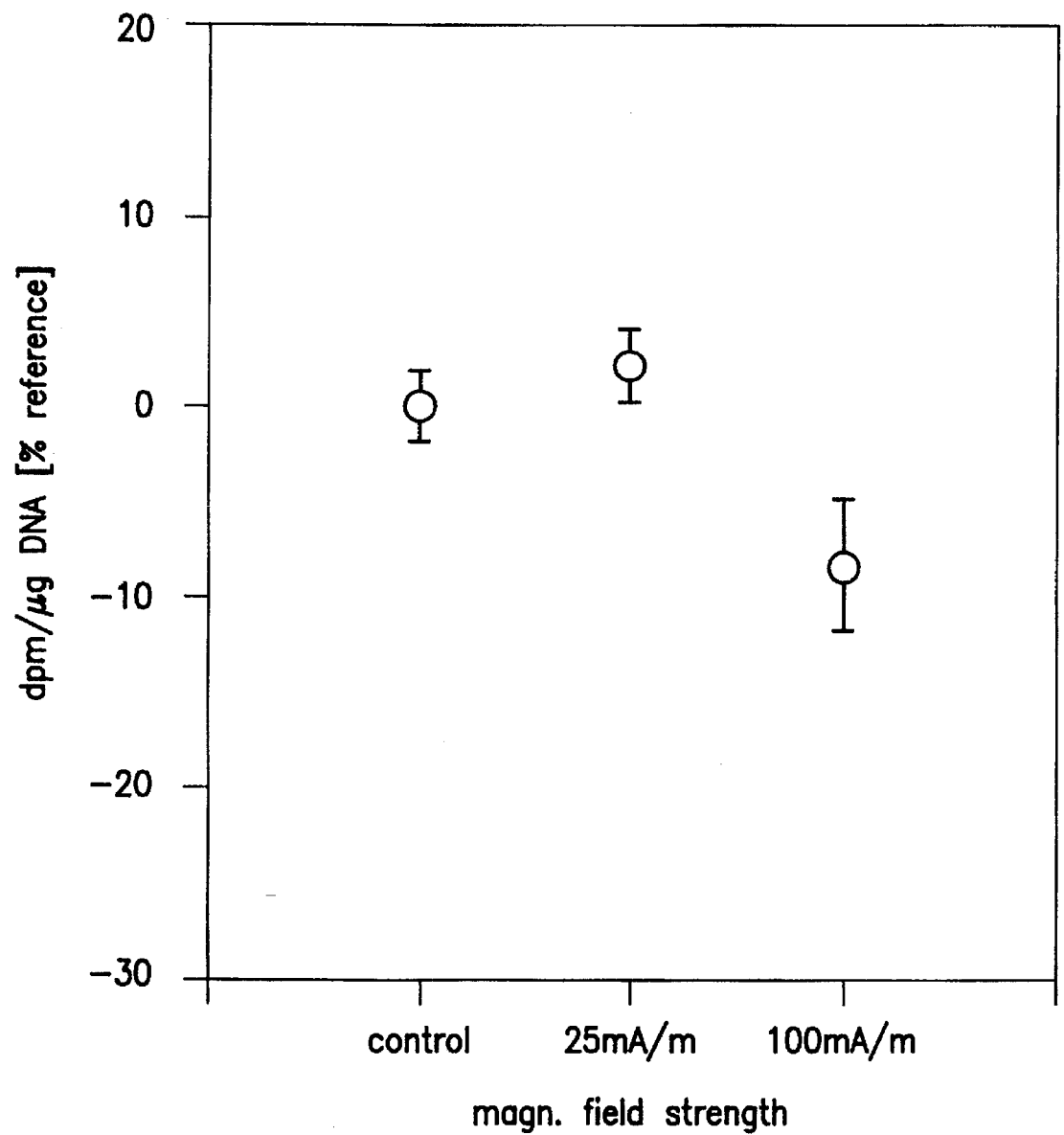
FIG. 3 is a plot of measured results concerning the influence exercised upon the proliferation rate of C6-glioma cells by irradiation with artificial atmospherics having a predominant frequency fraction of 10 kHz (atB)

The result has been represented in FIG. 3

Hence it appears that a small increase of the proliferation rate is at first obtained at low field strengths (25 mA/m), while at higher field strengths (100 mA/m) a significant reduction of the proliferation rate of DNA is observed.

The result indicates that certain spectra obtained by wideband reception of natural atmospherics have an influence on the proliferation activity of C6-glioma cells. The measurable influence obtained when producing artificial atmospherics indicates that natural atmospherics comprise radiation components which are not only indicators of biological effects but are the cause thereof.

2. Ascites-Hepatoma Rats

A further example of influencing the characteristics of a biological material is the irradiation of rats infected with an ascites hepatoma.

Yoshida tumor rats were used as testing objects. In these rats, Yoshida-ascites-rat hepatoma AH130 was generated by injecting the Yoshida cells. After intraperitoneal (i. p.) injection, the hepatoma developed within 11 to 14 days.

10 or respectively 20 ascites rats were irradiated with artificial atmospherics having a predominant frequency fraction of 10 kHz, the production of which has been described above. They were compared with 10 animals (control) having not been irradiated.

This comparison was carried out six times with artificial atmospherics having a spectral predominance of 10 kHz, at maximum field strength of 25 mA/m. In all six cases, the average survival time of the irradiated groups was longer than that of the control groups, namely by approx. 30%, starting from the day of first death.

In addition, this comparison was carried out another three times at maximum field strength of 100 mA/m. In all these three cases, the average survival time of the irradiated groups was shorter by approx. 30% than that of the control groups. The results have been represented in FIGS. 4(a) and 4(b).

Figure 4A:
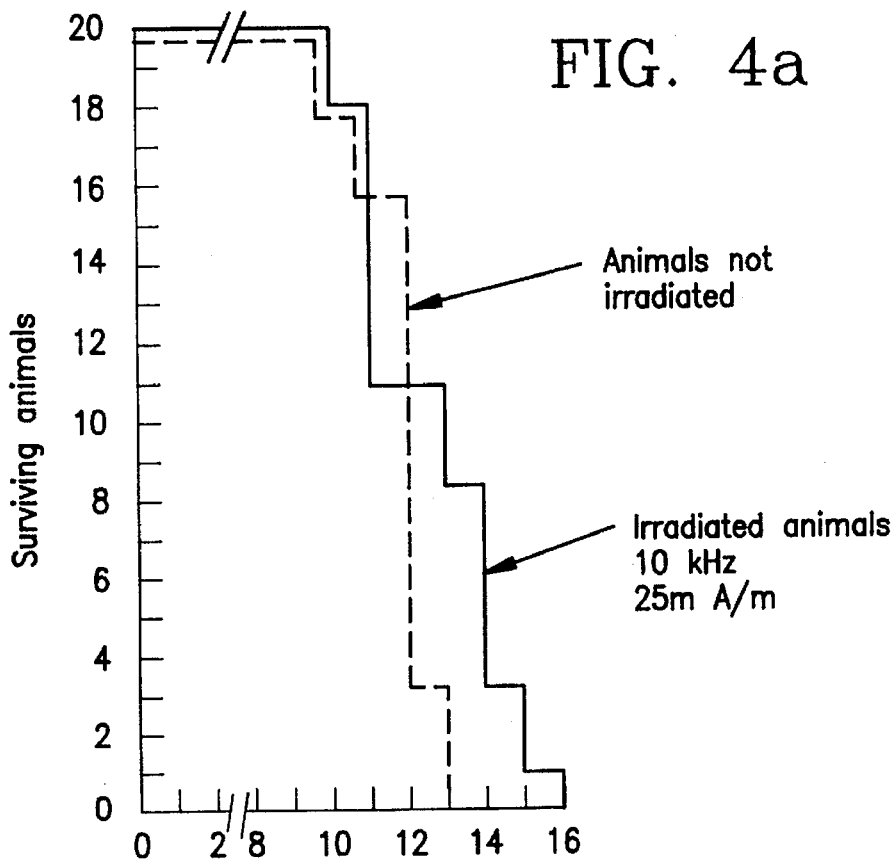
FIG. 4(a) shows the survival time of Yoshida tumor rats after/without irradiation with 10 kHz artificial atmospherics at a maximum field intensity of 25 mA/m.
Figure 4B:
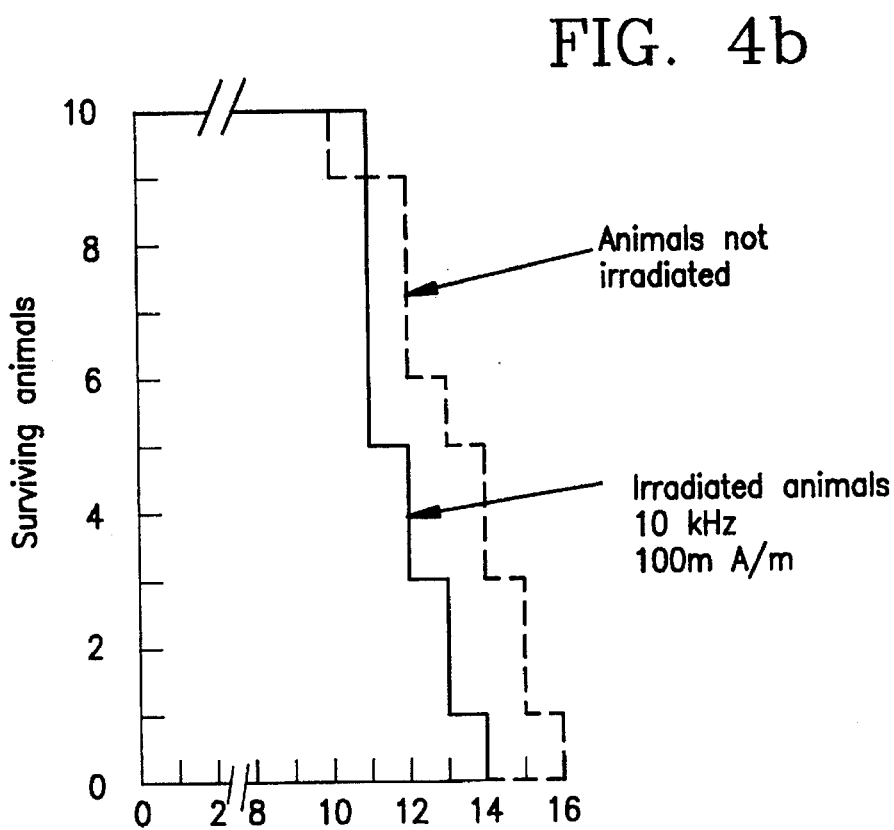
FIG. 4(b) is similar to FIG. 4(a), but at a maximum field intensity of 100 mA/m.

FIG. 4(a) shows the survival time of 20 Yoshida-asciteshepatoma rats after irradiation with 10 kHz atmospherics at a field strength of 25 mA/m. FIG. 4(b) shows the result at a field strength of 100 mA/m. The results for the control group having not been irradiated are represented in dot-dash lines, the results for the irradiated animals being represented in continuous lines.

It therefore appears that irradiation with low intensities (25 mA/m) increases the survival time of infected rats.

3. EEG Offset

Furthermore, one irradiation apparatus comprising two Helmholtz coils was designed in such a way as to allow total-body irradiation of human test persons. For this purpose, one of the Helmholtz coils was placed on a level with the mattress of a bed, the other coil being attached approx. 1 m higher. The test persons were laid on the bed, thereby exposing them to the fairly homogenous magnetic field of artificial atmospherics. About 20 healthy young persons were irradiated in this way, and a distinct offset in the EEG was observed. A typical result is given in FIG. 5. It shows the frequency spectrum of the EEG not influenced by atmospherics in dashed lines, and in continuous lines the EEG influenced by artificial atmospherics at a magnetic field strength of 25 mA/m and with a predominant frequency fraction of 8 kHz.

In particular, FIG. 5 shows printouts of autospectra obtained from the occipital EEG derivation of the test person. The dashed lines represent a 4-min section from a 10-min derivation with a patient, subdivided into 4 consecutive 4-min sections (1., 2., 3., 4.) taken approximately from the central part of the 10-min period and plotted on top of each other. The continuous lines represent the autospectrum of the same test person under irradiation with the magnetic field of 8 kHz at 25 mA/m. As compared with the zero derivation, a distinct offset can be observed in the faster portion of the dominating peak. The peaks in the very slow frequencies are mainly artifacts. A striking feature is the missing offset at 22 Hz. So the main change after irradiation takes place in the range of the so-called basic activity which, for both test persons, is in the $\alpha$-range (7.5–13.5 Hz). (Concerning the measuring method, cf. G. Ruhenstroth-Bauer, Intern. J. Neuroscience, in the press).

This result again proves—even for man—the efficiency of atmospherics rendered selectively controllable by means of the method and the apparatus of the present invention.

What is claimed is:

1. A method for influencing characteristics of a biological material as are correlated with the occurrence of natural atmospherics, the natural atmospherics having a magnetic-field associated therewith, comprising the steps of:

receiving and storing the variations over time of the magnetic-field of observed natural atmospherics;

generating artificial atmospherics by reproducing said stored magnetic-field of the observed natural atmospherics within a coil arrangement; and introducing biological material into the magnetic-field of the artificial atmospherics generated from the stored magnetic-field of the observed natural atmospherics.

2. The method of claim 1, wherein the observed natural atmospherics have pulses associated therewith and said pulses have a predominant frequency of 8 KHz.

3. The method of claim 1, wherein the observed natural atmospherics have pulses associated therewith and said pulses have a predominant frequency of 10 KHz.

4. The method of claim 1, wherein the biological material is infected with ascites hepatoma.

5. The method of claim 1, wherein the biological material is infected with tumor cells.

6. An apparatus for influencing biological and pathological parameters of a biological material, comprising:

a memory for storing signals representing the history of portions of observed natural atmospherics;

means connected to said memory for randomized readout of signals stored in said memory;

a magnetic-field generator connected to said means for randomized readout of signals stored in memory, for generating a magnetic-field representing artificial atmospherics from the signals readout of said memory, said magnetic-field generator having a magnetic-field associated therewith, the field strength of which is essentially homogeneous within a determined volume; and means within said magnetic field having the essentially homogeneous field strength for introducing a biological material into said magnetic-field having the essentially homogeneous field strength.

7. The apparatus of claim 6, wherein said magnetic-field generator comprises Helmholtz coils.

8. The apparatus of claim 6, wherein said magnetic-field generator comprises two coils situation above and below a surface adapted for receiving a test person thereon.

* * * * *